United States Patent
Hershey et al.

(10) Patent No.: US 7,732,135 B2
(45) Date of Patent: Jun. 8, 2010

(54) GENETIC MARKERS OF FOOD ALLERGY

(76) Inventors: Gurjit K. Khurana Hershey, 10264 Stablehand Dr., Cincinnati, OH (US) 45242; Amal Assa'ad, 9841 Gateclub Dr., Cincinnati, OH (US) 45241; Ranajit Chakraborty, 9182 Ambercreek Dr., Cincinnati, OH (US) 45237

( * ) Notice: Subject to any disclaimer, the term of this patent is extended or adjusted under 35 U.S.C. 154(b) by 858 days.

(21) Appl. No.: 10/566,903

(22) PCT Filed: Aug. 5, 2004

(86) PCT No.: PCT/US2004/025370

§ 371 (c)(1),
(2), (4) Date: Oct. 16, 2006

(87) PCT Pub. No.: WO2005/014861

PCT Pub. Date: Feb. 17, 2005

(65) Prior Publication Data

US 2007/0184441 A1    Aug. 9, 2007

Related U.S. Application Data

(60) Provisional application No. 60/492,507, filed on Aug. 5, 2003.

(51) Int. Cl.
*C12Q 1/68* (2006.01)
*C12P 19/34* (2006.01)

(52) U.S. Cl. .......................................... 435/6; 435/91.2

(58) Field of Classification Search ....................... None
See application file for complete search history.

(56) References Cited

FOREIGN PATENT DOCUMENTS

WO    WO 00/34789    6/2000

OTHER PUBLICATIONS

Howell et al. (Clinical and Experimental Allergy, 1998, vol. 28, pp. 156-162).*
Assa'ad et al., *Analysis of the R130Q IL-13 Polymorphism in Patients with Food Allergy*, Pediatric Research, 2001; 49 (4-2):11A (XP008040169).
Liu et al., *Associations between total serum IgE levels and the 6 potentially functional variants within the genes IL4, IL13, and IL4Rα in German children: The German Multicenter Atopy Study*, J Allergy Clin Immunol 2003; 112:382-388.
Mitsuyasu et al., *Ile50Val variant of IL4Rα upregulates IgE synthesis and associates with atopic asthma*, Nature Genetics 1998; 19:119-120.
PCT, *International Search Report*, PCT/US2004/025370, mailed Jan. 7, 2005, 7 pg.
Risma Ka et al., *V75R576 IL-4 Receptor α Is Associated with Allergic Asthma and Enhanced Il-4 Receptor Function*, J Immunol. 2002; 169:1604-1610.
Woo JG et al., *-159 C to T Polymorphism of CD14 is Associated with Non-Atopic Asthma and Food Allergy*, J Allergy Clin Immunol 2003; 111(2) Abstract Supplement:S127 (XP008040172).
Woo JG et al., *The -159 C->T polymorphism of CD14 is associated with nonatopic asthma and food allergy*, J Allergy Clin Immunol 2003. 112:438-444.

* cited by examiner

*Primary Examiner*—Juliet C Switzer
(74) *Attorney, Agent, or Firm*—Thompson Hine LLP

(57) ABSTRACT

A genetic marker of food allergy is disclosed. The marker comprises variants of IL-4 receptor alpha, IL13 and CD14.

5 Claims, No Drawings

SEQUENCE LISTING

<160> NUMBER OF SEQ ID NOS: 2

<210> SEQ ID NO 1
<211> LENGTH: 21
<212> TYPE: DNA
<213> ORGANISM: human

<400> SEQUENCE: 1
gtgccaacag atgaggttca c                                         21

<210> SEQ ID NO 2
<211> LENGTH: 22
<212> TYPE: DNA
<213> ORGANISM: human

<400> SEQUENCE: 2
gcctctgaca gtttatgtaa tc                                        22

GENETIC MARKERS OF FOOD ALLERGY

This application claims priority to U.S. Provisional Application 60/492,507 filed Aug. 5, 2003.

STATEMENT REGARDING FEDERALLY SPONSORED RESEARCH OR DEVELOPMENT

This invention was made with government support under Grant No. R01AI046652 awarded by the National Institutes of Health (NIH). The government has certain rights in the invention.

FIELD OF THE INVENTION

The invention is directed to functionally relevant genetic variants in three genes as a marker for food allergy.

BACKGROUND

Food allergy affects nearly 10% of all individuals. The estimated prevalence is 8% in the pediatric population and 2% in the adult population. Food allergy can be life-threatening; the primary therapy is avoidance of the allergenic food. Although the factors important in the pathogenesis of food allergy are not known, there is a genetic predisposition.

Class II HLA genotypes and a slow acetylation genetic variant of N-acetyltransferase 2 are associated with food allergy. Because food allergy occurs with higher frequency in individuals with other atopic disorders, including atopic dermatitis, asthma, and allergic rhinitis, some genes associated with atopy may be relevant in food allergy.

Interleukin (IL)-4 and IL-13 are Th2 cytokines that are critical for the development of allergic inflammation and have also been implicated in food allergy. IL-4 and IL-13 exert their effect through a common receptor, IL-4 receptor alpha (IL-4Rα). Genetic variants (polymorphisms) of IL-13, IL-4Rα, and CD14 have been implicated as atopy susceptibility genes. T cell clones specific to ovomucoid derived from egg-allergic subjects consistently expressed IL-5, IL-4, and IL-13. Patients with active atopic dermatitis and egg sensitivity had a marked increase in IL-4 synthesis by peripheral blood lymphocytes following in vitro stimulation with ovalbumin. Cells from patients with atopic dermatitis in remission had decreased IL-4 synthesis, comparable to that seen in normal individuals. Peripheral blood mononuclear cells from patients with food allergy had significantly increased IL-4 production following food challenge compared with IL-4 production prior to challenge.

CD 14 is a pattern recognition receptor that binds lipopolysaccharide (LPS) and other bacterial components. LPS binding to CD 14 activates antigen presenting cells, including macrophages and dendrtic cells, and subsequently releases proinflammatory cytokines and mediators. The gene for CD14 has been reported to contain several polymorphisms in its coding and promoter regions. One polymorphism, a C to T transition at position -159 (-159 C→T), has been shown to associate with atopy, but another study found no association of this CD 14 single nucleotide polymorphism (SNP) with asthma, atopic dermatitis, allergic rhinitis, total or specific IgE levels. The T allele, and particularly the TT genotype of the CD14-159 C→T polymorphism, is associated with food allergy.

Despite the similarities of food allergy with other atopic disorders, several characteristics of food allergy are distinct. Food allergy often presents very early in life, during the first few days or weeks while IgE responses are still immature. Thus, unlike other atopic disorders, food allergy is likely to be less dependent on mechanisms involving IgE. While sensitization to environmental allergens requires previous exposure of at least several years, sensitization to food allergens may occur after only one exposure or even in the absence of previous exposure. The early onset of food allergy indicates a role for innate immunity in its development.

Food challenge remains the gold standard for diagnosing food allergies, but has serious risks and potential complications. Additional alternative methods of determining a patient's propensity to food allergens are thus desirable.

SUMMARY OF THE INVENTION

An individual's propensity to a food allergy is determined by screening blood or other tissue for the presence of a marker gene that indicates an increased propensity for that individual to have or develop a food allergy. The marker genes include I75V, E400A, C431R, or Q576R in IL-4Rα, an enhanced TT (CD14 promoter-159 C→T), and R130Q in IL-13. In one embodiment, an excess of two-locus VV (I75V at IL-4Rα)-QR (R130Q at IL-13) and QR (R130Q at IL-13)-TT (at CD14-159 C→T) indicates the individual's increased propensity to a food allergy. In another embodiment, an allele combination comprising V75IL-4Rα/Q130IL-13/T159C→TCD14 indicates the individual's increased propensity to a food allergy. In another embodiment, a TT (CD14-159 C→T) genotype indicates the individual's increased propensity to a food allergy. At least a two locus analysis enhances association between an individual's genotype and food allergy phenotype. The markers may also determine the individual's propensity to an atopic condition such as eczema. Screening an infant may reduce or eliminate untoward effects of food allergens. Another embodiment is a genetic marker for a food allergy of a single nucleotide polymorphism in at least two of a V75 allele of a IL-4Rα gene, a Q130 allele of a IL-13 gene, and a T allele of a CD14 promoter. Another embodiment is a genetic marker for a food allergy that is a single nucleotide polymorphism -159 C→T in a CD14 promoter.

These and other advantages will be apparent in light of the following figures and detailed description.

DETAILED DESCRIPTION

The genetics of common single nucleotide polymorphisms (SNPs) in IL-4 receptor alpha (IL-4Rα), IL-13 and CD 14 were determined in patents with food allergy and in non-atopic, non-asthmatic control patients. A combination of genes important in innate immunity and the development of Th2 immunity and IgE may act together to promote the food allergy phenotype because of a complex interaction between the anti-inflammatory atopy-related cytokines IL-13 and IL-4 and the levels of expression of CD 14 on mononuclear cells and In soluble form, and/or because of other reasons. Combinations of allelic variants of these genes factored in food allergy. Four SNPs In IL-4Rα (I75V, E400A, C431R, Q576R), the R130Q IL-13 SNP, and the CD14-159 C→T promotor polymorphism were genotyped using PCR-based RFLP assays.

As will be subsequently analyzed, with each locus analyzed at the level of genotypes, the TT (CD14-159 C→T) genotype was associated with food allergy. However, no significant allele frequency difference between food allergy patients and normal controls was observed at any of the six polymorphic sites when analyzed individually. Sequential multi-locus analyses revealed significant excess of two-locus W (175V at IL-4Rα)-QR (R130Q at IL-13), and QR (R130Q at IL-13)-TT (at CD14-159 C→T) in food allergy patients compared to controls (p=0.029 and 0.011, respectively). This was caused by an increase of individuals carrying the allele combination of V75IL-4Rα, Q130IL-13, and T-159 C→TCD14 in patients with food allergy, compared to controls (p=0.008). Furthermore, this allele combination was associated with the phenotype of eczema among food allergy patients (p=0.02). The V75IL-4Rα/Q130IL-I3/T-159 C→TCD14 allele combination was associated with food allergy and may be used as a genetic marker to identify at risk infants and other patients.

Patients were recruited sequentially from the food allergy clinic at Cincinnati Children's Hospital Medical Center and also from a private allergist, and were offered to participate in the study if they had a confirmed diagnosis of food allergy. This was defined as a history of an immediate adverse reaction to a food with objective symptoms and signs and a positive prick skin test and/or radioallergosorbent test (RAST) to the food. Food challenges were done as indicated by the clinical history. A positive food challenge was taken as further confirmation of the diagnosis. The following information was collected during the clinical evaluation by a physician and/or from a questionnaire completed by the patient or caregiver(s) in the case of pediatric patients: A list of the food(s) that has/have caused an adverse reaction and, for each food listed, the following information: the age at which the first reaction occurred, a description of the reaction, the time between ingestion of the food and the onset of the reaction, whether the reaction was evaluated by a physician immediately or later, the method used to establish the diagnosis whether by prick skin tests and/or RAST, whether a food challenge was performed, whether the food had subsequently been eliminated from the diet, and whether the food was reintroduced in the diet any time later. Any co-existing allergic diseases such as asthma or eczema were identified. Eczema was diagnosed by history (a definite history of dry scaly skin and use of topical moisturizers and/or topical steroids) and/or physical exam. Because of the predominantly young age of the patient population and the difficulty in establishing the diagnosis of asthma in young patients, the diagnosis of asthma was not included in the analysis. Food reactions were classified as mild or severe according to the following definition. A severe reaction was defined as generalized anaphylaxis or a reaction that caused respiratory compromise, including angioneurotic edema endangering the airway. Cutaneous reactions and swelling of other parts of the face, e.g. the eyes, and mild vomiting were considered mild reactions.

Healthy, non-allergic, non-asthmatic, unrelated subjects were prospectively recruited from University of Cincinnati Medical Center and the Cincinnati Children's Hospital Medical Center. Individuals were excluded from this group if they reported a history of allergies, including food allergies, asthma, chronic cough or chronic obstructive pulmonary disease (COPD). The subjects underwent skin prick tests including positive and negative controls, and a panel of 14 common environmental antigens indigenous to the Ohio Valley (A.L.K. Laboratories Inc., Wallingford Conn.). Subjects with no positive skin prick tests, other than to the histamine, were included in the control group.

Skin prick tests were done to the food(s) that caused the initial adverse reaction(s) and to any other foods that have caused suspected adverse reactions. Skin prick tests were performed using commercially available extracts (Hollister Steer Laboratories, Spokane Wash.; Greer Laboratories, Lenoir N.C.) at a concentration of 1:10, 1:20 or 1:40 according to the manufacturer's instruction for each food extract. Histamine (1 mg/cc) was used for a positive control, and albumin saline was used as a negative control. The tests were read after fifteen minutes and interpreted by comparing the size of the wheal and flare to the positive and negative control as follows: 0=same size as negative control; 1+=very small induration, erythema present; 2+=50% of histamine control; 3+=same as histamine control; 4+=greater than histamine control or pseudopodia. Prick skin tests graded as 2+ or higher were considered positive. RAST tests were done at a commercial laboratory and RAST scores of 2 or higher were interpreted as positive.

Food challenges were performed on subjects who had no history of anaphylaxis to the food in question after consent was obtained. Challenges were performed as clinically indicated either at baseline to establish the diagnosis, or timed to establish resolution of the food allergy after a period of follow up. With the pediatric population, open challenges were performed by administering gradually increasing amounts of the food given at observed intervals dictated by the history (usually every 15 minutes). The challenge was performed on an empty stomach. A challenge was considered positive if any of the following objective signs were noted during the challenge or immediately after its completion: dermatologic signs, e.g. skin rash or edema; gastrointestinal, e.g, vomiting; or respiratory signs, e.g, sneezing, stridor or wheezing.

One hundred-ten patients with food allergy and 82 non-atopic control subjects were included. The demographic characteristics of the study participants are shown in Table 1.

TABLE 1

Demographic characteristics of Food allergy cases and Non-atopic control populations

| Population | | Food allergy cases (n = 110) | Non-atopic controls (n = 66) |
|---|---|---|---|
| Age ± SD [range] | | 6.3 ± 8.2 [0.48, 42.8] | 30.3 ± 7.7 [20, 54] |
| Sex | Male | 72.7% | 53% |
| | Female | 27.3% | 47% |
| Ethnicity | Caucasian | 81.8% | 83.3% |
| | African-American | 12.7% | 4.5% |
| | Asian | 2.7% | 6.1 |
| | Mixed | 0.9% | 0% |
| | Other | 0.9% | 3.03% |
| | Unknown | 0% | 3.03 |

The racial distribution of the population mirrors that of the Greater Cincinnati area from which patients and controls were drawn (2000 Census figures for Cincinnati Metropolitan Statistical Area, www.censusseope.org. accessed Feb. 11, 2003). Table 2 outlines the characteristics of the subjects with food allergy.

TABLE 2

Characteristics of Food Allergy Subjects

| | Number of subjects |
|---|---|
| Age at first reaction (Mean ± SD) | |
| Age <1 year (0.7 ± 0.2) | 58 |
| 1-2 years (1.7 ± 0.3) | 18 |
| 2-18 years (7.6 ± 4.3) | 11 |
| Age >18 years (31 ± 3.6) | 3 |
| TOTAL | 90 |

TABLE 2-continued

Characteristics of Food Allergy Subjects

| | Number of subjects |
|---|---|
| Association with eczema | |
| With eczema | 53 |
| Without eczema | 45 |
| Not known | 12 |
| TOTAL | 110 |
| Number of food allergies | |
| 1 | 53 |
| 2 | 31 |
| 3 | 14 |
| 4 | 9 |
| 5 | 3 |
| TOTAL | 110 |
| Food causing allergy | |
| Peanut | 59 |
| Milk | 38 |
| Egg | 37 |
| Fish | 13 |
| Soy | 10 |
| Wheat | 8 |
| Type of reaction | |
| Mild | 71 |
| Severe | 39 |
| TOTAL | 110 |

All patients had a diagnosis of IgE-mediated food allergy as previously defined. Of the 110 patients, 101 patients had a history of immediate adverse reaction and a positive prick skin test to one or more foods. Sixty-six of these patients also had positive RAST to one or more foods. Nine patients had a history of immediate adverse reaction to one or more foods that was confirmed by RAST only. In very few instances, particularly with peanut allergy, the diagnosis of an allergy to peanuts was made in the absence of a history of ingestion in a patient with an established diagnosis of food allergy to a different food. This was based on a positive skin test and/or RAST to peanuts, which were in the range that would predict a positive ingestion challenge. Forty-three patients had one or more food challenges with a total of 67 food challenges performed. Thirty-three of these patients (77%) had a clinical reaction to one or more food with a total of 47 positive food challenges.

The mean age at study entry was 6.3 years±8.2, and ranged from 0.48 to 42.8 years, with 30% of the patients being less than 2 years of age and a total of 93.6% of patients of pediatric age (<18 years). The age of the subject at the time of the first food allergy reaction (obtained from the history) paralleled the age at study entry with 84.5% of the first food allergy reactions occurring in patients less than 2 years of age.

There was a high prevalence of eczema in the patient population. Of 99 patients in whom the information was available, 54.5% had a diagnosis of eczema. Almost half the patients had an allergy to only one food, and about a third had an allergy to two foods. The patients had a total number of 208 food allergies. Of these, 28% were caused by peanuts, 18% by cow's milk, 18% by eggs, 6% by fish, 5% by soy and 4% by wheat. Additional allergenic foods that occurred with lower frequency included tree nuts, beef, chicken, pork, lobster, shrimp, lentils, strawberries and cantaloupe.

Genotyping of IL-4Rα, CD 14, and IL-13 SNPs was performed. Genomic DNA was isolated from EDTA anti-coagulated whole blood or from a buccal swab as described in Risma et al., V75R576 IL-4 receptor alpha is associated with allergic asthma and enhanced IL-4 receptor function, *J. Immunol* 169:1604-1610 (2002) which is expressly incorporated by reference herein. The IL-4Rα variants were genotyped as described in Risma. The following primers were used: sense 5'-GTGCCAACAGATGAGGTTCAC-3'; and antisense 5'-GCCTCTGACAGTTTATGTAATC-3' to determine the genotypes at the -159C→T CD14 SNP site. These primers amplified a 497 bp segment of the CD14 promoter from -517 to -19. An AvaII restriction site exists at position -159, such that the T allele is cut, resulting in bands of 144 and 353 bp, while the C allele remains uncut at 497 bp. After PCR amplification, the reaction volume was digested with 10 U of AvaII (New England Biolabs, Beverly Mass.) and restriction fragments were resolved on a 2% agarose gel. The IL-13 R130Q variant was genotyped as previously described in Graves, P. E., et al., A cluster of seven tightly linked polymorphisms in the IL-13 gene is associated with total senum IgE levels in three populations of white children, *J. Allergy Clin Immunol* 105:506-513 (2000) which is expressly incorporated by reference herein.

Conformity of genotype frequencies at each of the six sites with their respective Hardy-Weinberg expectations was tested by the goodness-of-fit chi-square test as described in Weir, B., *Genetic Data Analysis II*, Sunderland, Mass.: Sinauer Associates (1996) which is expressly incorporated by reference herein. Genotype/allele frequency differences between patients and controls were tested by the r by c contingency table test, with levels of significance empirically determined by the permutation test described in Roff, D. A. et al. The statistical analysis of mitochondrial DNA polymorphisms:chi 2 and the problem of small samples, *Mol Biol Evol* 6:539-545 (1989) which is expressly incorporated by reference herein. Ten thousand replications of permutation for each test were used.

Multi-locus association for food allergy was tested in two steps. First, allele Twenty-four combinations of six SNP sites showed that all observed genotypes were explained by 24 allele combinations (of the possible $2^6$=64), eight of which explained 72% of the genetic diversity in food allergy patients and 79% in the controls. These eight allele combinations were determined by genotypes at three sites, I75V at IL-4Rα, R130Q at IL-13, and C→T-159 CD14. This prompted investigation of food allergy associations involving three pairwise combinations of loci (I75V at IL-4Rα and R130Q at IL-13, I75V at IL-4Rα and CD14 -159 C→T, and R130Q at IL-13 and CD14-159 C→T) and one three-locus combination (I75V at IL-4Rα, R130Q at IL-13, and CD14-159 C→T). In the second step, for each of these tests, permutation-based levels of significance (with 10,000 replications) were determined for the respective r by c contingency tables. Genotype-combinations exhibiting significant frequency differences between food allergy patients and controls were examined to determine the specific set of allele combinations (at two- and three-locus levels) that explained the multi-locus genotype association with food allergy.

For the genotype:phenotype association analyses, the number of individuals carrying the specific combination of alleles was counted by classifying individuals into different categories of phenotypes. Frequency differences in such categorical data were tested by the r by c contingency table test previously described. When the phenotypes could be nominally ordered (e.g. age at first reaction), the trend test as described in Snedecor, G. et al., *Statistical Methods*, Iowa:

Iowa State University Press (1980) which is expressly incorporated by reference herein, was used to determine whether the proportion of patients carrying the specific three-locus allele combination increases with lower age of onset of allergy.

The individuals with food allergy and the control subjects were genotyped for six SNP sites in three different genes, IL-4RA (I75V, E400A, C431R, and Q576R), IL-13, and CD14. As shown In Table 3, all of the genetic markers were in Hardy-Weinberg equilibrium except for the IL-4Rα E400A in the cases (p=0.015).

TABLE 3

Genotype Frequency of IL-4Ra, IL-13 and CD 14 polymorphic variants in Individuals with Food Allergy and Non-atopic Controls

| Marker | Food Allergy Cases (n = 110) | Non-atopic Controls (n = 66) | p value |
|---|---|---|---|
| I75V IL-4Rα | II: 26 (0.236) IV: 56 (0.509) VV: 28 (0.254) — HWE: p = 0.846 | II: 17 (0.258) IV: 38 (0.576) VV: 11 (0.167) — HWE: p = 0.191 | 0.400 |
| E400A IL-4Rα | EE: 89 (0.809) EA: 17 (0.154) AA: 4 (0.036) — HWE: p = 0.015* | EE: 54 (0.818) EA: 11 (0.167) AA: 1 (0.015) — HWE: p = 0.618 | 0.797 |
| C431 R IL-4Rα | CC: 96 (0.873) CR: 13 (0.118) RR: 1 (0.009) — HWE: p = 0.463 | CC: 54 (0.818) CR: 12 (0.182) RR: 0 — HWE: p = 0.417 | 0.412 |
| Q576R IL-α | QQ: 65 (0.591) QR: 36 (0.327) RR: 9 (0.082) — HWE: p = 0.222 | QQ: 43 (0.652) QR: 20 (0.303) RR: 3 (0.045) — HWE: p = 0.732 | 0.566 |
| R130Q IL-13 | RR: 62 (0.564) RQ: 45 (0.409) QQ: 3 (0.027) — HWE: p = 0.119 | RR: 46 (0.697) RQ: 17 (0.258) QQ: 3 (0.045) — HWE: p = 0.394 | 0.117 |
| -159 C->T CD14 | CC: 36 (0.327) CT: 47 (0.427) TT: 27 (0.245) — HWE: p = 0.143 | CC: 23 (0.348) CT: 37 (0.561) TT: 6 (0.09 1) — HWE: 0.103 | 0.036* (for TT: p = 0.015*) |

HWE = Hardy Weinberg Equilibrium

Genotype frequencies of the CD14-159C→T site were significantly different between allergy cases and controls (p=0.036). This was due to an increase of the CD14 TT genotype in patients with food allergy with the odds ratio of 3.523 (95% CI: 1.265<OR<8.369).

An increased frequency of the TT genotype at the CD14-159 C→T locus in patients with food allergy implicated CD 14 in the genetics of food allergy. Because food allergy is a complex multi-factorial disease and because association of CD14 was not significant at the level of alleles (i.e., "C" vs. "T" frequency difference, p=0.118), multiple genes were examined. The allele combination of all six SNP sites was first examined, showing that eight out of twenty-four allele combinations explained 72% of the genetic diversity in patients with food allergy and 79% of the genetic diversity in normal controls. These eight allele combinations were determined by genotypes at three sites I75V at IL-4Rα, R130Q at IL-13, and 159 C→T at CD14.

Investigation of food allergy association was then conducted focusing on these SNPs at the two-locus level and three-locus level. At the two-locus level, frequencies of genotype WQR (between I75V at IL-4Rα and R130Q at IL-13) and genotype QRTT (between R130Q at IL-13 and 159 C→T at CD14) were significantly higher in patients with food allergy than normal controls, with p value of 0.029 and 0.011 respectively as shown in Table 4, odds ratio for genotype VVQR was 4.109 (95% CI: 1.161<OR<14.537), and for genotype QRTT was 10.263 (95% CI: 1.323<OR<79.618).

TABLE 4

Genotype frequency difference in food allergy patients and controls at two-locus level.

| | Frequency | |
|---|---|---|
| Genotype | Cases | Controls |
| I75V IL-4Rα and R130Q IL-13 | | |
| IIQQ | 1 (0.009) | 1 (0.015) |
| IVQQ | 2 (0.018) | 2 (0.030) |
| VVQQ | 0 (0.000) | 0 (0.000) |
| IIQR | 4 (0.036) | 6 (0.091) |
| IVQR | 23 (0.209) | 8 (0.121) |
| VVQR | 18 (0.164) | 3 (0.045) |
| IIRR | 21 (0.191) | 10 (0.152) |
| IVRR | 31 (0.282) | 28 (0.424) |
| VVRR | 10 (0.091) | 8 (0.121) |
| P-value* | | |
| overall | 0.073 | |
| specific | Genotype VVQR: 0.029 | |
| R130Q IL-13 and CD14 159C → T | | |
| QQCC | 2 (0.018) | 0 (0.000) |
| QRCC | 10 (0.091) | 8 (0.121) |
| RRCC | 24 (0.218) | 15 (0.227) |
| QQCT | L (0.009) | 3 (0.045) |
| QRCT | 20 (0.182) | 8 (0.121) |
| RRCT | 26 (0.236) | 26 (0.394) |
| QQTT | 0 (0.000) | 0 (0.000) |
| QRTT | 15 (0.136) | I (0.015) |
| RRTT | 12 (0.109) | 5 (0.076) |
| P-value* | | |
| overall | 0.024 | |
| specific | genotype QRTT: 0.011 | |

*P-value was obtained by 10,000 replicates of permutation.

At the three-locus level, there were eight individuals carrying the genotype of VV (I75V at IL-4Rα)-QR (R130Q at IL-13)-TT (CD14) in patients with food allergy, and 0 in normal controls (p=0.054).

Further investigation was done to determine whether the combination of these three loci associated with food allergy (Table 5).

TABLE 5

3-locus genotype frequency difference in food allergy patients and controls at 3-locus level.

| 3-Locus | Cases | | Controls | |
|---|---|---|---|---|
| VV-QR-CC | 3 | (0.027) | 1 | (0.015) |
| VV-QR-CT | 7 | (0.064) | 2 | (0.030) |
| VV-QR-TT | 8 | (0.073) | 0 | (0.000) |
| VV-RR-CC | 2 | (0.018) | 2 | (0.030) |
| VV-RR-CT | 5 | (0.046) | 5 | (0.076) |
| VV-RR-TT | 3 | (0.027) | 1 | (0.015) |
| IV-RR-CC | 12 | (0.109) | 9 | (0.136) |
| IV-RR-CT | 13 | (0.118) | 16 | (0.242) |
| IV-RR-TT | 6 | (0.055) | 3 | (0.046) |
| IV-QQ-CC | 1 | (0.009) | 0 | (0.000) |
| IV-QQ CT | 1 | (0.009) | 2 | (0.030) |
| IV-QR-CC | 6 | (0.055) | 4 | (0.061) |

TABLE 5-continued 3-locus genotype frequency difference in food allergy
patients and controls at 3-locus level.

| 3-Locus | Cases | | Controls | |
|---|---|---|---|---|
| IV-QR-CT | 11 | (0.100) | 4 | (0.061) |
| IV-QR-TT | 6 | (0.055) | 0 | (0.000) |
| II-QQ-CC | 1 | (0.009) | 0 | (0.000) |
| II-QQ-CT | 0 | (0.000) | 1 | (0.015) |
| II-QR-CC | 1 | (0.009) | 3 | (0.046) |
| II-QR-CT | 2 | (0.018) | 2 | (0.030) |
| II-QR-TT | 1 | (0.009) | 1 | (0.015) |
| II-RR-CC | 10 | (0.091) | 4 | (0.061) |
| II-RR-CT | 8 | (0.073) | 5 | (0.076) |
| II-RR-TT | 3 | (0.027) | 1 | (0.015) |
| P-value | | | | |
| overall | | 0.325 | | |
| specific | | genotype VV-QR-TT: 0.054 | | |

* These 3 loci are: I75V at IL-4Ra, R130Q at IL-13, and CD14 −159 C → T.
P-value was obtained by 10,000 replicates of permutation.

Two allele combinations could be derived from genotype VV-QR-TT, one was V-Q-T, and the other was V-R-T. Thirty-three patients with food allergy carried the specific allele combination V-Q-T, versus eight patients in the normal control group (p=0.008, odds ratio was 3.107, 95% CI: 1.336<OR<7.228). The number of individuals carrying the V-R-T allele combination was not significantly different between patients with food allergy and controls.

The specific allele combination of V (I75V at IL-4Rα)-Q (R130Q at IL-13-T (CD14) constituted the major genetic predisposition underlying food allergy determined in the study. The combination of genetic variants in all three genes was superior to a single gene or to two genes together. The Q576R IL-4Rα allele, strongly associated with atopy and atopic asthma, was examined to determine its effect in combination with any combination of the other allelic variants of IL-4Rα, IL-13 and CD14 in food allergy; no significant associations were found.

Any significant genotype:phenotype relationships among the food allergy patients were evaluated. The number of individuals carrying the. specific combination of alleles was counted by classifying individuals into different categories of phenotypes as shown in Table 6.

TABLE 6

Association of V75 IL-4Ra/Q130 IL-13/T -159C → T
CD14 Genetic Haplotype with Food Allergy Phenotypes

| Association with eczema | N | Number (%) of subjects with haplotype | p value |
|---|---|---|---|
| Controls | 66 | 0(0%) | p < 0.0001 |
| Food Allergy patients | 110 | 33(30%) | |

| | N | Number of subjects with haplotype | p value |
|---|---|---|---|
| Age at first reaction (Mean .-t SD) | | | |
| Age <1 year (0.7 ± 0.2) | 58 | 20(34.5%) | p = 0.187 |
| 1-2 years (1.7 .t 0.3) | 18 | 5(25%) | |
| 2-18 years (7.6 ± 4.3) | 11 | 1(9.09%) | |
| Age >18 years (31 ± 3.6) | 3 | 0(0%) | |
| Association with eczema | | | |
| With eczema | 53 | 22(41.5%) | p = 0.020 |
| Without eczema | 45 | 8(17.7%) | |

TABLE 6-continued

Association of V75 IL-4Ra/Q130 IL-13/T -159C → T
CD14 Genetic Haplotype with Food Allergy Phenotypes

| Number of food allergies | | | |
|---|---|---|---|
| 1 | 53 | 18(33.9%) | p = NS |
| 2 | 31 | 8(25.8%) | |
| 3 | 14 | 4(28.6%) | |
| 4 | 9 | 3(33.3%) | |
| 5 | 3 | 0(0%) | |
| Food causing allergy | | | |
| Peanut | 59 | 21(35.6%) | p = NS |
| Milk | 38 | 12(31.6%) | |
| Egg | 37 | 13(35.1%) | |
| Fish | 13 | 3(23.1%) | |
| Soy | 10 | 0(0%) | |
| Wheat | 8 | 1(12.5%) | |
| Type of reaction | | | |
| Mild | 71 | 25(35.2%) | p = 0.164 |
| Severe | 39 | 8(20.5%) | |

NS = not significant

The presence of the specific allele combination was associated with eczema (p=0.010). Patients with food allergy and eczema (n=53) had a prevalence of 41.5% carrying the specific allele combination, which was significantly higher when compared to 17.7% in patients with food allergy without eczema (p=0.017). Thus, the association of the allele combination was stronger among patients with food allergy and eczema. For the phenotype "age at first reaction", the previously described trend test examined whether the frequency of patients carrying the V75IL-4Rα/Q130IL-13/T-I59C→T combination increased with a lower age at the time of the first food allergy reaction. The proportion of patients carrying the specific allele combination was increased among patients with a lower age of onset of food allergy (p=0.018). No significant relationship was noted between the individuals carrying the specific allele combination and the number of food allergies, reaction severity, or a particular food.

The data demonstrated the association between a specific combination of allelic variants in three different genes, CD 14, IL-4RA, and IL-13, and food allergy. Specifically, the combination of the V75 allele of the IL-4Rα, coupled with Q130 IL-13 and the T allele of -159C→T of CD14 alone was a genetic marker for food allergy. All three of these genetic variants have been shown to be functionally relevant, resulting in enhanced expression or activity of their respective gene products. The combination of these three variant alleles exhibited a stronger association with food allergy than any of these individual alleles. At a single site level, significant association of the T-159 C→T CD 14 allele, and especially of the TT genotype, with food allergy was observed. However, the combination of this allele with the IL-4Ra and IL-13 atopy-associated variants resulted in a much stronger significant association.

The consequences of SNPs in multiple genes in combination may provide additional information. A given SNP may only be relevant in the context of a second or a combination of additional SNPs in the same gene or other genes as shown for a combination of IL-4Rα allelic variants. Furthermore, a given SNP may have no effect individually or in combination with a different set of SNPS. Genetic association studies may be difficult to interpret due to poor reproducibility in other populations. One reason for this may be that a given genetic variant may not be important unless it is examined in the context of one or more additional SNPs, contributing to disparate results in different populations.

IL-4Rα is a necessary signaling component of the IL-13 receptor complex, such that atopy-associated genetic variants in IL-13 and IL-4RA may act in a concerted fashion, as supported by interactive genetic effects between SNPs in IL-4Ra and the IL-13 promotor. However, the mechanisms underlying the association of the IL-13/IL-4Ra pathway with CD14 is less obvious. Interactions between CD 14 and IL-4 have been described. While bacterial products such as LPS activate monocytes and increase CD 14 expression, IL-4, which has anti-inflammatory properties, downregulates CD 14 expression. An LPS-induced increase in CD 14 expression rescued monocytes from apoptosis, whereas IL-4 treatment resulted in decreased CD14 expression and eventual apoptosis. Down-regulation or removal of CD 14 triggered apoptosis, whereas up-regulation promoted survival of monocytes. Interactions between CD14 and IL-13 have also been reported. Similar to the previously described effect of IL-4, IL-13 down-regulated CD14 by suppressing CD 14 RNA expression. Furthermore, in a segmental antigen challenge model, soluble CD14 levels correlated with IL-13 concentrations 18 h after the challenge. Thus, IL-4 and IL-13, which both signal via IL-4Rα, have direct effects on CD14 expression, and this may contribute to the mechanism by which genetic variants of these three genes act together to promote food allergy.

In considering the roles of membrane and soluble CD 14 in atopic diseases, a complex of LPS and LPS-binding protein in the serum initiates signals in monocytes and macrophages via membrane CD 14. However, soluble CD 14 can also Initiate signals, thus cells lacking CD 14 can also respond to LPS. LPS, acting through its receptor complex Including CD14, TLR4, and MD-2 induced maturation of antigen presenting cells (APC) including dendritic cells and macrophages. Increased CD 14 expression would result In increased LPS binding and increased production of proinflammatory mediators by monocytes and macrophages including prostaglandins, reactive oxygen and nitrogen intermediates, IL-1, IL-6, IL-8, TNFα, and IL-12. The T allele was shown to result in approximately 32% increased transcriptional activity of the promoter when compared with the C allele and the mechanism of this association was related to alterations in transcription factor binding to this region. Thus, this SNP may be associated with alterations In CD 14 expression, and the relative ratios of soluble and membrane CD 14. Soluble CD 14 levels are higher in asthmatics than non-asthmatic controls. In the present invention, the T allele, which is associated with increased transcriptional activity, had increased frequency among subjects with food allergy.

An allele associated with an increase in transcription of CD 14 correlated with the presence of food allergy, especially when combined with functionally relevant genetic variants of IL-13 and IL-4Rα. While not bound by any particular theory, the mechanism for this association may be that the LPS in foods acts as an adjuvant and increases the specific IgE response to foods in susceptible individuals. The IL-13 and IL-4Rα allelic variants would contribute to the IgE response. Alternatively, an increased pro-inflammatory response in the gut secondary to the presence of the T CD 14 allele, increased CD 14 production, and resultant increased inflammatory cytokine production, may be associated with an enhanced sensitization to food allergens, especially early in life. The association may be the result of direct interplay between IL-4, IL-13 and CD 14 that determines the final contribution of CD 14 pathways by modulating total as well as soluble and membrane CD 14 levels.

Early identification of infants at-risk for developing food allergies is desirable. Earlier initiation of therapeutic interventions may attenuate or delay the phenotype. The genetic marker may identify certain phenotypes among food allergy patients; for example, the data demonstrated a significant association with atopic dermatitis among patients with food allergy. The genetic marker identified may identify a subgroup of patients with a specific pattern of response to a food, and may predict positive challenges. This may make food challenge unnecessary in some cases. Furthermore, the combination genotype may be predictive of a specific natural history or response to therapy and aid in the management of food allergy.

From among the study participants, an analysis was made of genetic markers of food allergy and specific genes associated with allergy to a particular food (i.e., peanut or milk). The analysis was limited to Caucasians, which constituted the predominant ethnic group in the study, and is presented in Tables 7 and 8.

TABLE 7

Study Participants and Specific Food Allergies

| # | Race | Gender | I75V | E400A | C431R | Q576R | S786P | IL-13 R130Q | −159 C→T | Allergic Foods |
|---|------|--------|------|-------|-------|-------|-------|-------------|----------|----------------|
| 1 | White | Male | II | EE | CC | QQ | SS | QQ | CC | fish (trout) |
| 2 | White | Female | IV | AA | CR | RR | SS | RR | CT | cantaloupe blueberries |
| 3 | White | Male | IV | EE | CC | QR | SS | RR | CT | milk |
| 4 | White | Male | IV | EE | CC | QQ | SS | RR | TT | egg milk |
| 5 | White | Male | VV | EE | CR | QR | SS | RR | CC | milk |
| 6 | White | Female | IV | EE | CC | QQ | SS | RR | CT | tree nuts (hazelnut, cashew, almond, walnut), milk, peanut, soy |
| 7 | White | Male | II | EA | CC | QR | SS | RR | CC | milk, soy, egg, wheat, corn |
| 8 | White | Male | II | EE | CC | QQ | SS | RR | CT | milk, egg |
| 9 | White | Female | IV | EE | CC | QQ | SS | RQ | CC | milk, egg, walnut, peanut |
| 10 | White | Male | IV | EE | CC | QQ | SS | RQ | CC | peanut |
| 11 | White | Male | IV | EE | CC | QR | SS | RQ | CT | milk |
| 12 | White | Female | II | EE | CC | QQ | SS | RQ | TT | egg, soy |
| 13 | White | Male | IV | AA | RR | RR | SS | RR | CC | peanut, soy |

TABLE 7-continued

Study Participants and Specific Food Allergies

| # | Race | Gender | I75V | E400A | C431R | Q576R | S786P | IL-13 R130Q | −159 C→T | Allergic Foods |
|---|------|--------|------|-------|-------|-------|-------|-------------|----------|----------------|
| 14 | White | Male | IV | EE | CC | QQ | SS | RR | CC | milk, egg, soy, peanut, fish |
| 15 | White | Male | II | EE | CC | QR | SS | RR | CT | milk, egg, wheat, walnut |
| 16 | White | Male | IV | EE | CC | QR | SS | RR | TT | peanut, almonds, lentils, peas |
| 17 | White | Female | VV | EE | CC | QR | SS | RQ | CT | peanut, walnut, egg, milk |
| 18 | White | Male | II | EE | CC | QQ | SS | RR | CC | milk |
| 19 | White | Male | IV | EE | CC | QQ | SS | RQ | CT | walnut |
| 20 | White | Female | VV | EE | CR | QR | SS | RQ | CC | lobster, shrimp |
| 21 | White | Male | II | EE | CC | QQ | SS | RR | CT | egg, milk, peanut |
| 22 | White | Female | IV | EE | CR | RR | SS |  | CT | peanut, milk, egg, chocolate, banana, peaches, strawberry, tomato |
| 23 | White | Male | IV | EE | CC | QR | SS | RQ | CC | peanut |
| 24 | White | Female | VV | EE | CC | QQ | SS | RQ | TT | peanut |
| 25 | White | Male | II | EE | CC | QR | SS | RR | TT | milk |
| 26 | White | Male | VV | EE | CC | QQ |  | RR | CT | egg, wheat, peanut |
| 27 | White | Male | VV | EE | CC | QQ |  | RQ | CC | milk, peanut, wheat, soy corn, fish, egg |
| 28 | White | Female | VV | EE | CR | QR |  | RQ | TT | peanuts |
| 29 | White | Female | IV | EE | CC | QQ |  | RR | CC | peanut, cashew, pecan, walnut |
| 30 | White | Male | IV | EE | CC | QQ |  | RQ | CT | peanut |
| 31 | White | Male | IV | EE | CC | QQ |  | RR | CC | milk |
| 32 | White | Female | II | EE | CC | QQ |  | RR | CC | peanut, walnut |
| 33 | White | Male | II | EE | CC | QQ |  | RR | CT | peanut |
| 34 | White | Male | VV | EE | CR | QR |  | RR | TT | milk |
| 35 | White | Male | IV | EE | CC | QQ |  | RR | CC | milk, peanut |
| 36 | White | Male | VV | EE | CR | QR |  | RQ | TT | milk, egg, peanut, wheat |
| 37 | White | Female | II | EE | CC | QQ |  | RR | CT | peanut, pecans, hazelnut |
| 38 | White | Female | VV | EE | CC | QR |  | RQ | CT | milk |
| 39 | White | Male | IV | EE | CC | QR |  | RR | CC | milk, peanut, egg, tree nuts |
| 40 | White | Male | IV | EE | CC | QQ |  | RR | TT | egg |
| 41 | White | Male | IV | EE | CR | QR |  | RR | CT | milk, egg, peanut, wheat, soy, lima beans |
| 42 | White | Female | IV | EE | CC | QR |  | RR | CT | clams, fish |
| 43 | White | Male | II | EA | CC | QQ |  | RR | TT | cashews |
| 44 | White | Male | VV | EE | CC | QQ |  | RQ | CT | eggs, milk, peanut |
| 45 | White | Male | IV | EE | CC | QR |  | RR | CC | peanut |
| 46 | White | Female | IV | EE | CC | QQ |  | RQ | TT | turkey/chicken |
| 47 | White | Male | II | EA | CR | QR |  | RR | CT | peanut |
| 48 | White | Female | II | EA | CR | QR |  | RR | CC | peanut |
| 49 | White | Female | IV | EA | CR | QR |  | RR | CT | peanut |
| 50 | White | Male | VV | EE | CC | QQ |  | RR | TT | milk, sweet potato, eggs, peas, fish |
| 51 | White | Male | II | EA | CC | QR |  | RR | TT | peanut, egg |
| 52 | White | Male | IV | EE | CC | QQ |  | RQ | CT | milk, egg, peanut |
| 53 | White | Male | IV | EE | CC | QQ |  | RQ | CT | peanut |
| 54 | White | Male | VV | EA | CR | QR |  | RR | CT | wheat |
| 55 | White | Female | IV | EE | CC | QQ |  | RQ | CC | walnut, egg |
| 56 | White | Female | IV | EE | CC | QQ |  | RR | CT | milk, eggs, wheat |
| 57 | White | Male | IV | EE | CC | QQ |  | RR | CT | pecan, english walnut |
| 58 | White | Male | VV | EA | CC | QQ |  | RQ | CC | peanut |
| 59 | White | Male | IV | EE | CC | QQ |  | RR | CC | peanut |
| 60 | White | Male | IV | EE | CC | QQ |  | RQ | CC | peanut |
| 61 | White | Male | IV | EE | CC | QQ |  | RQ | CT | peanut |
| 62 | White | Male | IV | EE | CC | QQ |  | RQ | CT | peanut |
| 63 | White | Male | IV | EE | CC | QQ |  | RR | CC | milk, wheat, eggs, peanut |
| 64 | White | Female | IV | EE | CC | QQ |  | RQ | TT | walnut |
| 65 | White | Male | IV | EE | CC | QQ | SS | RR | CC | peanut |
| 66 | White | Male | IV | EE | CC | QR | SS | RR | CT | pistachio, milk |
| 67 | White | Male | IV | EE | CC | QR | SS | QQ | CC | egg, peanut, strawberry |
| 68 | White | Female | II | EE | CC | QQ | SS | RR | CC | sesame seed, milk, peanut, wheat, egg |
| 69 | White | Male | IV | EE | CC | QQ | SS | RQ | TT | tree nuts |
| 70 | White | Male | II | EE | CC | QQ | SS | RR | CT | fish |
| 71 | White | Male | VV | EE | CC | QQ | SS | RR | TT | peanut |
| 72 | White | Male | VV | EE | CC | QQ | SS | RQ | TT | peanut, milk |
| 73 | White | Male | VV | EE | CC | QQ | SS | RQ | TT | milk |
| 74 | White | Male | VV | EA | CR | RR |  | RQ | TT | egg, milk, peanut |
| 75 | White | Male | IV | EE | CC | QQ | SS | RQ | TT | egg, fish, beef, peanut |

TABLE 7-continued

Study Participants and Specific Food Allergies

| # | Race | Gender | I75V | E400A | C431R | Q576R | S786P | IL-13 R130Q | -159 C→T | Allergic Foods |
|---|------|--------|------|-------|-------|-------|-------|-------------|----------|----------------|
| 76 | White | Male | IV | EE | CC | QQ | | RR | CT | mollusks, shellfish |
| 77 | White | Male | IV | EE | CC | QR | | RQ | CC | peanut, milk, wheat |
| 78 | White | Male | IV | EE | CC | QR | | RR | TT | egg, peanut, fish |
| 79 | White | Male | II | EE | CC | QR | | RQ | CC | peanut, egg |
| 80 | White | Male | IV | EE | CC | QQ | | QQ | CT | egg, peanut |
| 81 | White | Male | II | EE | CC | QQ | | RR | CT | peanut |
| 82 | White | Male | II | EE | CC | QQ | | RR | CC | peanut |
| 83 | White | Male | IV | EE | CC | QQ | | RR | CC | peanut, milk, eggs, spinach |
| 84 | White | Male | VV | EE | CC | OO | | RR | CT | cashew, pecan, walnut |
| 85 | White | Male | II | EE | CC | QR | | RR | CC | chicken, turkey |
| 86 | White | Male | II | EE | CC | QQ | | RR | CC | almonds |
| 87 | White | Male | VV | EE | CC | QQ | | RQ | TT | peanut |
| 88 | White | Male | VV | EE | CC | QQ | | RR | CT | fish |
| 89 | White | Male | VV | EE | CC | QQ | | RQ | TT | peanuts, milk, sunflower seeds. |
| 90 | White | Female | IV | EA | CC | QQ | | RR | CC | tree nut |

TABLE 8

Normal Controls

| Sample# | Race | Gender | I75V | E400A | C431R | Q576R | S786P | IL-13 R130Q | -159 C→T |
|---------|------|--------|------|-------|-------|-------|-------|-------------|----------|
| 1 | White | Male | II | EE | CC | QQ | SS | RR | CT |
| 2 | White | Female | IV | EA | CR | QR | SS | RR | CC |
| 3 | White | Female | VV | EE | CC | QQ | SS | RR | CT |
| 4 | White | Female | II | EE | CC | QQ | SS | RR | CT |
| 5 | White | Male | IV | EE | CC | QQ | SS | RR | CT |
| 6 | White | Female | IV | EE | CC | QQ | SS | RR | TT |
| 7 | White | Male | IV | EE | CC | QR | SS | RR | CT |
| 8 | White | Male | VV | EE | CC | QR | SP | RR | TT |
| 9 | White | Male | II | EE | CC | QQ | SS | RR | TT |
| 10 | White | Male | IV | EE | CC | QQ | SS | RR | CT |
| 11 | White | Male | IV | EE | CC | QR | SS | RR | CC |
| 12 | White | Male | II | EA | CR | QR | SS | RQ | CT |
| 13 | White | Male | II | EE | CC | QQ | SS | RR | CC |
| 14 | White | Male | IV | EE | CR | QR | SS | RQ | CT |
| 15 | White | Male | IV | EE | CC | QR | SS | RR | CC |
| 16 | White | Female | IV | EE | CC | QQ | SS | RQ | CC |
| 17 | White | Male | II | EE | CC | QQ | SS | RR | CT |
| 18 | White | Female | IV | EE | CC | QR | SS | RQ | CT |
| 19 | White | Male | VV | EE | CC | QQ | SS | RR | CT |
| 20 | White | Female | IV | EE | CC | QR | SS | RR | CT |
| 21 | White | Male | VV | EE | CC | QQ | SS | RQ | CT |
| 22 | White | Male | IV | EE | CC | QQ | SS | RR | CC |
| 23 | White | Female | IV | EE | CC | QQ | SS | QQ | CT |
| 24 | White | Female | IV | EE | CC | QR | SS | RR | CC |
| 25 | White | Male | II | EA | CR | QR | SS | RQ | CT |
| 26 | White | Male | IV | EA | CR | QR | SS | RQ | CC |
| 27 | White | Male | II | EA | CR | QR | SS | RR | CC |
| 28 | White | Female | IV | EE | CC | QR | SS | RR | CC |
| 29 | White | Female | II | EE | CC | QQ | SS | RQ | CC |
| 30 | White | Male | IV | EE | CC | QQ | SS | RR | CC |
| 31 | White | Female | II | EE | CC | QQ | SS | RQ | CC |
| 32 | White | Male | IV | EE | CC | QR | SP | RR | CT |
| 33 | White | Female | VV | EE | CC | QQ | SS | RQ | CC |
| 34 | White | Male | IV | EE | CC | QQ | SS | RR | CT |
| 35 | White | Female | II | EE | CC | QQ | SS | RR | CC |
| 36 | White | Male | IV | EA | CR | QR | SS | RQ | CC |
| 37 | White | Female | VV | EE | CC | QQ | SS | RQ | CT |
| 38 | White | Male | IV | EE | CC | QQ | SS | RR | CT |
| 39 | White | Male | II | EE | CC | QQ | SS | RQ | CC |
| 40 | White | Male | IV | EE | CC | QQ | SS | RR | CT |
| 41 | White | Female | VV | EA | CR | QR | SS | RR | CT |
| 42 | White | Male | II | EE | CC | QQ | SS | RQ | TT |
| 43 | White | Female | IV | EE | CC | QQ | SS | RR | CT |
| 44 | White | Female | IV | EE | CC | QQ | SS | RR | CC |
| 45 | White | Male | IV | EE | CC | RR | SS | RR | CT |
| 46 | White | Female | IV | EE | CC | QQ | | RQ | CT |
| 47 | White | Female | II | EE | CC | QQ | | RR | CT |
| 48 | White | Female | IV | EE | CC | QQ | | RR | CT |

TABLE 8-continued

Normal Controls

| Sample# | Race | Gender | I75V | E400A | C431R | Q576R | S786P | IL-13 R130Q | -159 C→T |
|---|---|---|---|---|---|---|---|---|---|
| 49 | White | Female | VV | EE | CC | QQ | | RR | CT |
| 50 | White | Female | VV | EE | CC | QQ | | RR | CC |
| 51 | White | Female | IV | EA | CR | QR | | QQ | CT |
| 52 | White | Male | II | EE | CC | QQ | | RR | CT |
| 53 | White | Female | IV | EA | CR | QR | | RR | CT |

Based upon the analysis, significant genetic combinations were associated with food allergy and with peanut and/or milk. Among patients with food allergy, homozygous mutant type TT (-159C→T) is more common among patients than in controls, and no other combination of markers shows more associations. Between peanut allergy patients (a subgroup of the whole food allergy cases) and normal controls, the specific combination VV(I75V)-RQ(IL13 R130Q)-TT(-159C→T) is more common in peanut allergy patients, meaning the combination of these three markers associates with peanut allergy. Between milk allergy patients (again a subgroup of the whole food allergy cases), the combination of VV(I75V)-TT(-159C→T) again is more commen among milk allergy patients. Because the markers VV(I75V), RQ(IL13 R130Q), and TT(-159C→T) locate at different genes, the specific combinations show association with peanut allergy and milk allergy, respectively, that may be regarded as evidence of gene-gene interaction.

Other variations or embodiments of the invention will also be apparent to one of ordinary skill in the art from the above figures and descriptions. For example, using cells obtained by a buccal swab In a kit test configured and formulated by routine methods known to one skilled in the art, the markers may be readily determined. Thus, the forgoing embodiments are not to be construed as limiting the scope of this invention.

---

---

What is claimed is:

1. A method of determining an individual's propensity to a peanut allergy, the method comprising
   screening nucleic acid of the individual for the presence of a combination of markers which results in QR at position 130 of the polypeptide of IL-13, VV at position 75 of the IL-4Rα polypeptide, and TT at position -159 of the CD 14 promoter, and
   identifying the individual as having an increased propensity to a peanut allergy if the combination of markers is present.

2. A method of determining an individual's propensity to a milk allergy comprising
   screening nucleic acid of the individual for the presence of a combination of markers which results in VV at position 75 of the IL-4Rα polypeptide and TT at position -159 of the CD 14 promoter, and
   identifying the individual as having an increased propensity to a milk allergy if the combination of markers is present.

3. A method to determine an individual's propensity to a food allergy, the method comprising
   determining the presence of an allele combination comprising a genotype which results in V at polypeptide position 75 of IL-4Rα, Q at polypeptide position 130 of IL-13, and T at nucleotide position -159 of CD14 promoter in at least one cell in the individual, wherein the presence of the allele combination indicates the individual's increased propensity to a food allergy.

4. The method of claim 3 further determining the individual's propensity to eczema.

5. The method of claim 3 wherein the individual is an infant.

* * * * *